United States Patent [19]

Wandell

[11] Patent Number: Plant 7,120

[45] Date of Patent: Jan. 23, 1990

[54] *FRAXINUS PENNSYLVANICA* LEDNAW

[76] Inventor: Willet N. Wandell, Rte. #1 Box 286, Ocuawka, Ill. 61469

[21] Appl. No.: 252,498

[22] Filed: Oct. 3, 1988

[51] Int. Cl.[4] ..... A01H 5/00

[52] U.S. Cl. ..... Plt./51

[58] Field of Search ..... Plt./51

[56] References Cited

PUBLICATIONS

Johnson, H. (1973), "The Ashes of North America and Europe", *Trees,* Simon and Schuster Inc., N.Y., pp. 238 and 239.

Preston, R. J., (1950), "Oleaceae", *North American Trees,* The Iowa State College Press, Ames, Iowa, p. 349.

Wyman, D., (1965), "*Fraxinus pennsylvanica lanceolata*", *Trees for American Gardens,* MacMillan Publishing Co., N.Y., p. 243.

Fernald, M. L., (1950), "3.*F. pennsylvanica* Marsh", *Gray's Manual of Botany,* American Book Co., N.Y., pp. 1148 and 1149.

Elias, T. S., (1980), "Green Ash", *Trees of North America,* Outdoor Life/Nature Books, N.Y., pp. 865 and 866.

*Primary Examiner*—James R. Feyrer

[57] ABSTRACT

This new varietal sport of *Fraxinus pennsylvanica* summit green ash has been produced asexually from a sport branch of 'Summit' green ash (*Fraxinus pennsylvanica* 'Summit') found growing on a tree at Madison, Wis. with the characteristic of many lateral branches growing from a main branch or limb axis. Propagation by me asexually from this sport produced vigorous straight-growing trees with a strong central leader, an adnormally high number of lateral branches, many appearing at three inch intervals on the main stem. These laterals grew in a strongly ascending manner producing semi-lustrous dark green foilage, turning yellow in the fall, and tree crown with a ratio of 15 to 20% of the height in width, much narrower than asexual progeny of Summit ash of the same age and size.

4 Drawing Sheets

BACKGROUND OF INVENTION

This new sport of *Fraxinus pennsylvanica* Summit green ash was found growing at Madison, Wis. in 1985, cultivated in clay soil in a rolling terrain area. This sport-supporting growth showed intense close branching and exceptional vigor. Both of these characteristics were exhibited in progeny produced by asexually reproduction of material obtained from the parent tree. I have 100 asexually produced trees of this sport by chip budding in my nursery at Oquawka, Ill., and all exhibit uniform prolific branching, short internodes and upright growth habit.

SUMMARY OF INVENTION

A new and distinct cultivar of *Fraxinus pennsylvanica* characterized by prolific branching at an early age, short internodes and an upright character of growth approximately ¼ crown width of *Fraxinus pennsylvanica,* 'Summit', from which the sport was discovered and taken.

DESCRIPTION OF THE NEW PLANT

Figure 1:
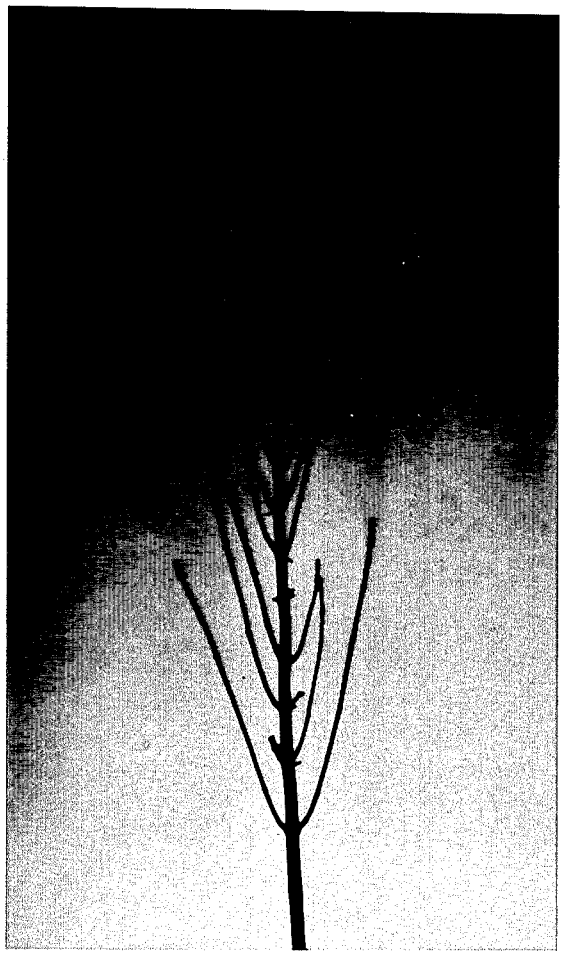
FIG. 1: Discloses the heavy, tight branch arrangement of a two year old specimen of the new variety.
Figure 2:
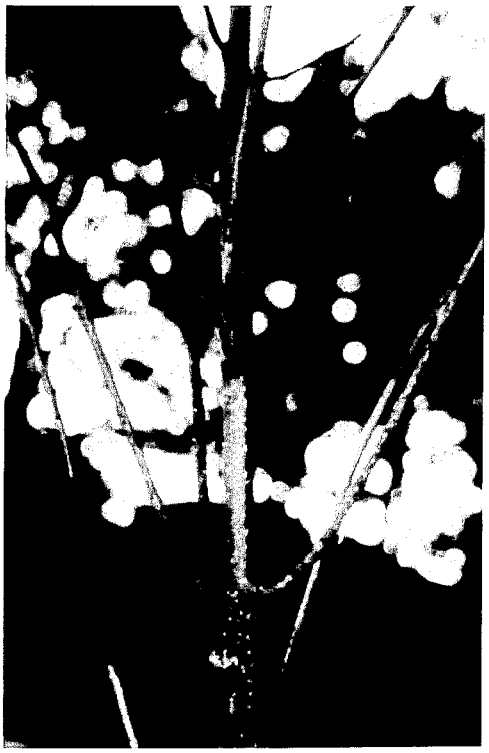
FIG. 2: Showing the emergence of the limbs, at an angle of 45 degrees to 60 degrees and then ascending in a strong overlapping manner.
Figure 3:
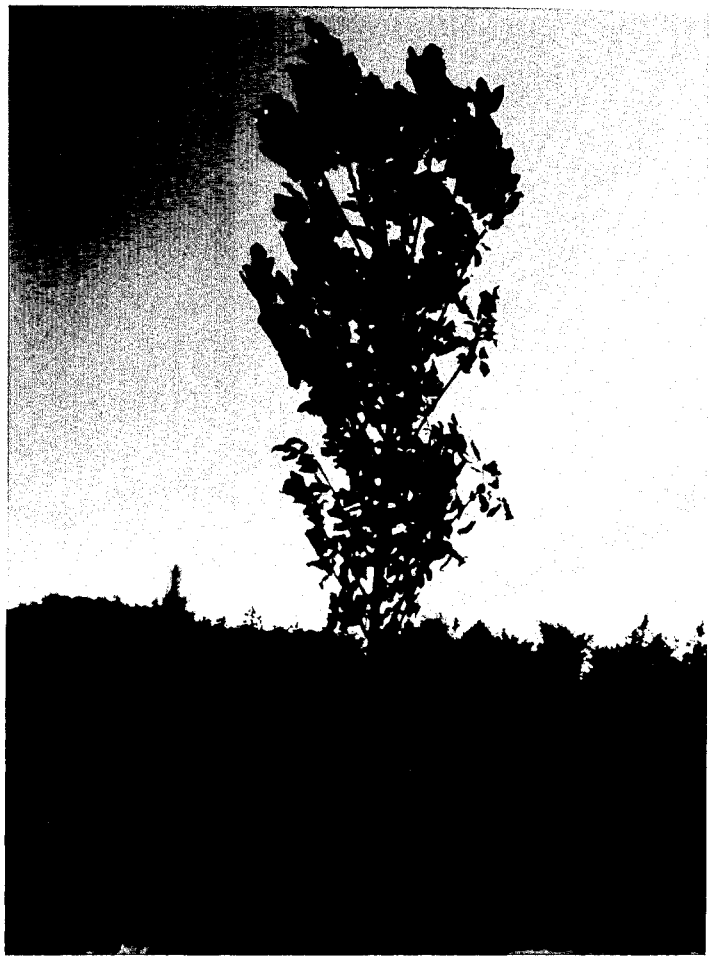
FIG. 3: Showing a three year old tree of the new variety in foilage displaying the strong, narrow, upright habit of growth.
Figure 4:
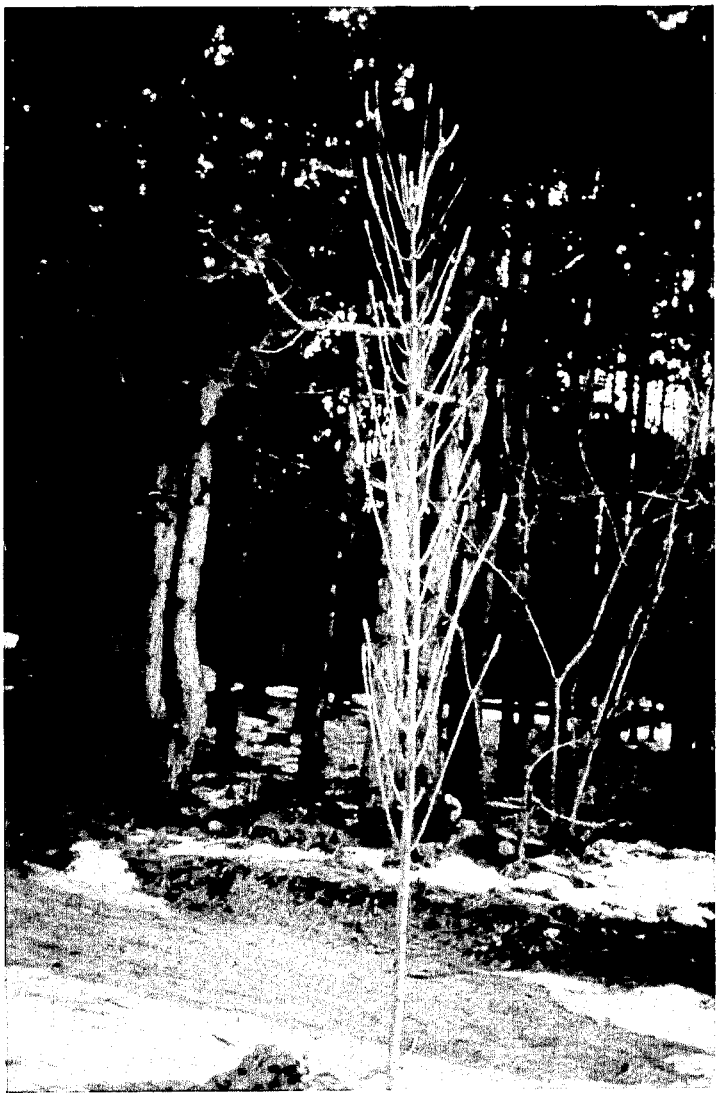
FIG. 4: Silhouettes the upright growth habit on a two year old tree of the new variety.
Figure 5:
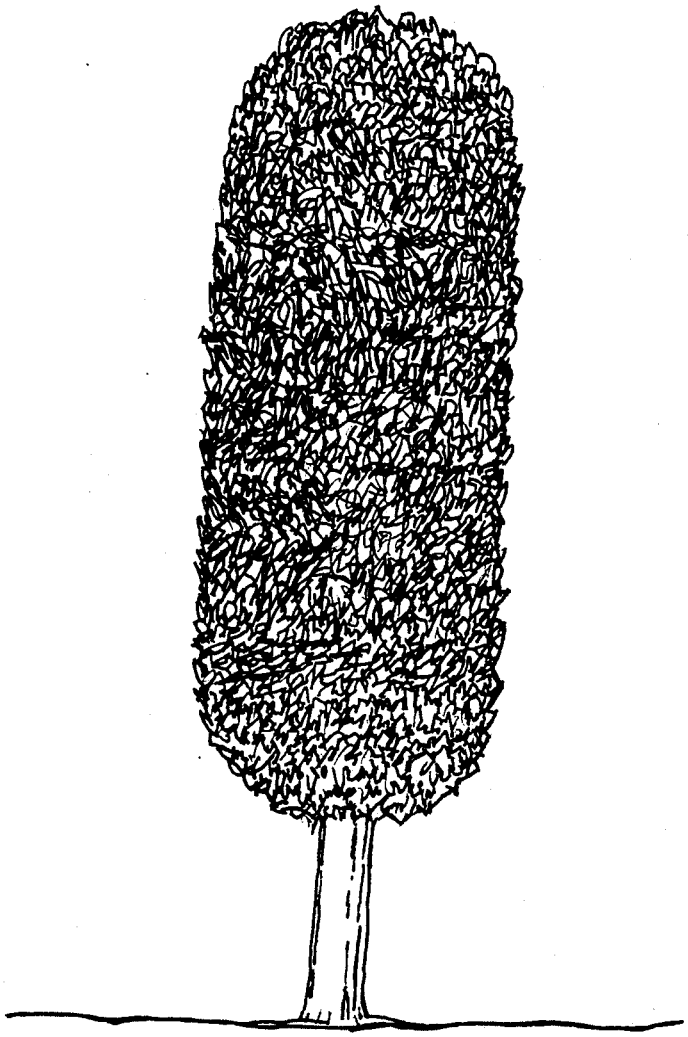
FIG. 5: A hand drawing showing the reasonably expected older specimen shape.

The following is a detailed description of my new variety of *Fraxinus pennsylvanica* green ash with color designations according to the R.H.S. Colour Chart published by The Royal Horticultural Society of London, England and the stated observations having been made on trees growing in Oquawka, Ill. by the applicant and found to distinguish from the species.

Origin: A branch sport of summit green ash *Fraxinus pennsylvanica* found in a cultivated area in park-like conditions in southern Wisconsin as a sport of a green ash seedling.

Classification: *Fraxinus pennsylvanica.*

Parentage: A sport of green ash.

Form: Moderate sized upright tree, branch spread 15–20 degree of the height.

Habit: Deciduous tree with a single trunk and a straight, single leader; crown strongly fastigiate, narrowly oval in shape. Heavily upright branches form from the main stem from nodes at close intervals.

Twigs: Stout, 3.5–7 mm is diameter, round, slightly swollen at the nodes, marked with raised, round lenticels; first year stems straite, glabrous, lustrous, medium brown; older twigs loosing striations, glabrous, becoming matt, gray; leaf scars opposite, semicircular, nearly straight across the top, 4 mm broad on first year stems, with numerous bundle traces arranged in a C-shaped pattern.

Winter buds: Reddish-brown, 3 mm long, half-globose, with 2 or 3 pairs of opposite, over-lapping bud scales, densely covered with tiny adpressed peltate scales; terminal bud present, broadly ovoid; stipule scars lacking.

Bark: Gray-brown, longitudinally furrowed.

Leaves: Opposite, pinnately compound with mostly 5 leaflets, sometime 7 or 3; radicals glaucous, grooved on the upper surface, the groove puberulent within; leaflets narrowly ovate, 6–13 cm long and 2–4 cm broad, deep green and semi-lustrous above (RHS 139A), paler and matte below (RHS 146B), turning yellow in autumn, glabrous, the apices acuminate, the margins consistently with rounded teeth, the bases cuneate; petiolules pubescent at the base, those of lateral leaflets 1–2 mm long, those of terminal leaflets 15–25 mm long.

Flowers: Dioecious, only staminate flowers present, produced in dense clusters from lateral buds; petals absent; calyx very reduced, less than 0.5 mm long; anthers 2.4 mm long, the filaments 1 mm long.

Fruit: Not observed, plant with only staminate flowers.

Fall color: Strong yellow mid-season in the fall.

The variety of sport-origin clearly distinguishes itself from other observed green ashes in its prolific branch habit producing branches at close interval which emerge at 45 degrees to 60 degrees but soon assume a strong upright growth posture over-lapping branches more distal. Leaves are narrow ovate, borne in abundance and turn a strong yellow mid-season in the fall.

I claim:

1. A new and distinctive variety of *Fraxinus pennsylvanica* named 'Lednaw', as described and illustrated herein, that differs from all other varieties by the unique combination of: (1) very narrow colunmar growth habit; (2) dense symmetrical crown due to closely spaced, strongly ascending branches that overlap each other; and (3) leaves dark green and semi-lustrous above, paler below, turning yellow in autumn.

* * * * *